United States Patent [19]
Laurencin et al.

[11] Patent Number: 5,766,618
[45] Date of Patent: Jun. 16, 1998

[54] POLYMERIC-HYDROXYAPATITE BONE COMPOSITE

[75] Inventors: Cato T. Laurencin, Somerville, Mass.; Jessica Devin, Sunnyvale, Calif.; Muhammed Attawia, Watertown, Mass.

[73] Assignee: Massachusetts Institute of Technology, Cambridge, Mass.

[21] Appl. No.: 811,582

[22] Filed: Mar. 5, 1997

Related U.S. Application Data

[62] Division of Ser. No. 222,539, Apr. 1, 1994, Pat. No. 5,626,861.

[51] Int. Cl.$^6$ ................................ A61F 2/02; A61K 9/50
[52] U.S. Cl. ............................................ 424/426; 424/501
[58] Field of Search ................................ 424/426, 501

[56] References Cited

U.S. PATENT DOCUMENTS 5,383,931  1/1995  Hehli et al. ................................ 623/16

*Primary Examiner*—Carlos Azpuru
*Attorney, Agent, or Firm*—Arnall Golden & Gregory, LLP

[57] ABSTRACT

A method for the fabrication of three-dimensional macroporous polymer matrices for use as bone graft or implant material was developed. The composites are formed from a mixture of biodegradable, biocompatible polymer and hydroxyapatite (HA), a particulate calcium phosphate ceramic. The method leaves irregular pores in the composite between 100 and 250 microns in size. In a preferred embodiment, implants are composed of a 50:50 poly (lactide-co-glycolide) (PLGA) polymer and reinforced by hydroxyapatite. Mechanical and histological analysis showed the matrix fabricated by this method to be structurally and mechanically similar to cancellous bone. Prior to degradation, pure polymer specimens exhibited an elastic modulus of 293 MPa and specimens which were 50% HA by weight exhibited a modulus of 1459 MPa. After six weeks of degradation under physiological conditions, the reinforcing effect of ceramic loading had diminished. Modulus of polymer matrices at all HA load levels had decreased sharply to approximately 10 MPa. Mean macro- and micropore diameters of the polymer specimens were 100 µm and 20 µm respectively and remained constant throughout degradation.

12 Claims, 2 Drawing Sheets

POLYMERIC-HYDROXYAPATITE BONE COMPOSITE

This is a divisional of U.S. Ser. No. 08/222,539, filed on Apr. 1, 1994 now U.S. Pat. No. 5,626,861.

The United States government has certain rights in this invention by virtue of government support under Grant Number 911170-BCS awarded by the National Science Foundation.

BACKGROUND OF THE INVENTION

The present invention is generally in the area of polymeric implants for bone repair and replacement, and particular is a polymer-hydroxyapatite composite.

Successful design of an implant to replace skeletal tissue requires knowledge of the structure and mechanical properties of bone and an understanding of the means by which grafts become incorporated into the body. This information can then be used to define desirable characteristics of the implant to ensure that the graft functions in a manner comparable to organic tissue.

The mechanical properties of bone are related to the internal organization of the material, as reviewed by Roesler, H., "The History of Some Fundamental Concepts in Bone Biomechanics," *Journal of Biomechanics*, 20, 1025–34 (1987). Cortical bone is classified as a material of less than 30% porosity, as described by Keaveny, T. M. and W. C. Hayes, "Mechanical Properties of Cortical and Trabecular Bone," in *Bone Volume 7: Bone Growth-B*, B. K. Hall, ed., Boca Raton: CRC Press, 285–344 (1992), as a "solid containing a series of voids (Haversian canals, Volkmann's canals, lacunae and canaliculi). The porosity of cortical bone tissue (typically 10%) is primarily a function of the density of these voids." In contrast, cancellous/trabecular bone is "a network of small, interconnected plates and rods of individual trabeculae with relatively large spaces between the trabeculae." Trabecular bone has a porosity of 50–90% which is a function of the space between the trabeculae.

The material properties of bone are based on determinations of the elastic modulus, compressive and tensile strengths. As a general rule, bone is stronger in compression than in tension and cortical is stronger than trabecular bone. Ranges of reported elastic modulus have been from 10 MPa to 25 GPa (10 MPa to 2 GPa for cancellous bone; 4 to 25 GPa for cortical and cancellous bone); compressive strength between 40 and 280 MPa (40 to 280 MPa for cancellous bone; 138 to 193 MPa for cortical bone); and tensile strength between 3.5 MPa and 150 MPa (3.5 to 150 MPa for cancellous bone; 69 to 133 MPa for cortical bone) (Friedlaender and Goldberg, *Bone and Cartilage Allografts* Park Ridge: American Academy of Orthopedic Surgeons 1991; Jarcho, "Calcium Phosphate Ceramics as Hard Tissue Prosthetics" *Clin. Orthopedics and Related Research* 157, 259–278 1981; Gibson, "The Mechanical Behavior of Cancellous Bone" *J. Biomechan.* 18(5), 317–328 1985; Keaveny and Hayes 1992).

Mechanisms by which bone may fail include brittle fracture from impact loading and fatigue from constant or cyclic stress. Stresses may act in tension, compression, or shear along one or more of the axes of the bone. A synthetic bone substitute must resist failure by any of these stresses at their physiological levels. A factor of safety on the strength of the implant may ensure that the implant will be structurally sound when subject to hyperphysiological stresses.

A graft may be necessary when bone fails and does not repair itself in the normal amount of time or when bone loss occurs through fracture or tumor. Bone grafts must serve a dual function: to provide mechanical stability and to be a source of osteogenesis. Since skeletal injuries are repaired by the regeneration of bone rather than by the formation of scar tissue, grafting is a viable means of promoting healing of osseous defects, as reviewed by Friedlaender, G. E., "Current Concepts Review: Bone Grafts," *Journal of Bone and Joint Surgery*, 69A(5), 786–790 (1987). Osteoinduction and osteoconduction are two mechanisms by which a graft may stimulate the growth of new bone. In the former case, inductive signals of little-understood nature lead to the phenotypic conversion of connective tissue cells to bone cells. In the latter, the implant provides a scaffold for bony in growth.

The bone remodeling cycle is a continuous event involving the resorption of pre-existing bone by osteoclasts and the formation of new bone by the work of osteoblasts. Normally, these two phases are synchronous and bone mass remains constant. However, the processes become uncoupled when bone defects heal and grafts are incorporated. Osteoclasts resorb the graft, a process which may take months. More porous grafts revascularize more quickly and graft resorption is more complete. After graft has been resorbed, bone formation begins. Bone mass and mechanical strength return to near normal.

Present methods for the repair of bony defects include grafts of organic and synthetic construction. Three types of organic grafts are commonly used: autografts, allografts, and xenografts. An autograft is tissue transplanted from one site to another in the patient. The benefits of using the patient's tissue are that the graft will not evoke a strong immune response and that the material is vascularized, which allows for speedy incorporation. However, using an autograft requires a second surgery, which increases the risk of infection and introduces additional weakness at the harvest site. Further, bone available for grafting may be removed from a limited number of sites, for example, the fibula, ribs and iliac crest. An allograft is tissue taken from a different organism of the same species, and a xenograft from an organism of a different species. The latter types of tissue are readily available in larger quantities than autografts, but genetic differences between the donor and recipient may lead to rejection of the graft.

Synthetic implants may obviate many of the problems associated with organic grafts. Further, synthetics can be produced in a variety of stock shapes and sizes, enabling the surgeon to select implants as his needs dictate, as described by Coombes, A. D. A. and J. D. Heckman, "Gel Casting of Resorbable Polymers: Processing and Applications," *Biomaterials*, 13(4), 217–224 (1992). Metals, calcium phosphate ceramics and polymers have all been used in grafting applications.

Calcium phosphate ceramics are used as implants in the repair of bone defects because these materials are non-toxic, non-immunogenic, and are composed of calcium and phosphate ions, the main constituents of bone (Jarcho, 1981; Frame, J. W., "Hydroxyapatite as a biomaterial for alveolar ridge augmentation," *Int. J. Oral Maxillofacial Surgery*, 16, 642–55 (1987); Parsons, et al."Osteoconductive Composite Grouts for Orthopedic Use," *Annals N.Y. Academy of Sciences*, 523, 190–207 (1988)). Both tricalcium phosphate (TCP) $[Ca_3(PO_4)_2]$ and hydroxyapatite (HA) $[Ca_{10}(PO_4)_6(OH)_2]$ have been widely studied for this reason. Calcium phosphate implants are osteoconductive, and have the apparent ability to become directly bonded to bone, as reported by Jarcho 1981. As a result, a strong bone-implant interface is created.

Calcium phosphate ceramics have a degree of bioresorbability which is governed by their chemistry and material structure. High density HA and TCP implants exhibit little resorption, while porous ones are more easily broken down by dissolution in body fluids and resorbed by phagocytosis. However, TCP degrades more quickly than HA structures of the same porosity in vitro. In fact, HA is relatively insoluble in aqueous environments.

Use of calcium phosphates in bone grafting has been investigated because of the chemical similarities between the ceramics and the mineral matrix found in the teeth and bones of vertebrates. This characteristic of the material makes it a good candidate as a source of osteogenesis. However, the mechanical properties of calcium phosphate ceramics make them ill-suited to serve as a structural element. Ceramics are brittle and have low resistance to impact loading.

Biodegradable polymers are used in medicine as suture and pins for fracture fixation. These materials are well suited to implantation as they can serve as a temporary scaffold to be replaced by host tissue, degrade by hydrolysis to non-toxic products, and be excreted, as described by Kulkarni, et al., *J. Biomedical Materials Research*, 5, 169–81 (1971); Hollinger, J. O. and G. C. Battistone, "Biodegradable Bone Repair Materials," *Clinical Orthopedics and Related Research*, 207, 290–305 (1986). Four polymers widely used in medical applications are poly(paradioxanone) (PDS), poly(lactic acid) (PLA), poly(glycolic acid) (PGA), and PLAGA copolymers. Copolymerization enables modulation of the degradation time of the material. By changing the ratios of crystalline to amorphous polymers during polymerization, properties of the resulting material can be altered to suit the needs of the application. For example, PLA is crystalline and a higher PLA content in a PLAGA copolymer results in a longer degradation time, a characteristic which may be desirable if a bone defect requires structural support for an extended period of time. Conversely, a short degradation time may be desirable if ingrowth of new tissue occurs quickly and new cells need space to proliferate within the implant.

Coombes and Heckman 1992 and Hollinger 1983 have attempted to create poly(lactide-co-glycolide) [$(C_3H_4O_2)_x$ $(C_2H_2O_2)_y$] implants as bone substitute. Hollinger used a PLAGA of high inherent viscosity (0.92 dl/g) prepared by a solvent-non-solvent casting method. Plugs of this material were implanted in tibial defects of Walter Reed rats, and humoral defects were created as control sites in which no polymer was implanted. Examination of the defects after sacrifice of the animals at 7, 14, 21, 28 and 42 days suggested that polymer may aid in osteoinduction in the early bone repair process. However, by 42 days, the rate of repair was equivalent in controls and experimental defect sites. Coombes and Heckman described a gel casting method for producing a three-dimensional PLAGA matrix. Success of this method, i.e., creation of a strong, rubbery gel, was dependent upon high inherent viscosity of the polymer (0.76–0.79 dl/g). Material properties of the polymer matrix through a degradation cycle were the focus of the research. The modulus of the PLAGA implant before degradation was 130 MPa, equivalent to that of cancellous bone. After eight weeks degradation in phosphate buffered saline (PBS), the strength of the material had deteriorated significantly. Moreover, the microporous structure (pores 205 μm in diameter) has been shown to be too small to permit the ingrowth of cells, as reported by Friedlaender and Goldberg 1991 and Jarcho 1981. From a mechanical as well as a biological standpoint, this matrix is not ideal for use as a substitute bone graft material.

It is therefore an object of the present invention to provide a matrix, and method for making the matrix, which is useful as a bone graft.

It is a further object of the present invention to provide a matrix which provides both mechanical stability and serves as a source of osteogenesis over the time period required for bone replacement.

SUMMARY OF THE INVENTION

A method for the fabrication of three-dimensional macroporous polymer matrices for use as bone graft or implant material was developed. The composites are formed from a mixture of biodegradable, biocompatible polymer and hydroxyapatite (HA), a particulate calcium phosphate ceramic. The method leaves irregular pores in the composite between 100 and 250 microns in size. In a preferred embodiment, implants are composed of a 50:50 poly (lactide-co-glycolide) (PLGA) polymer and reinforced by hydroxyapatite. The mechanical strength of the matrix is comparable to that of bone prior to and after several weeks degradation. The polymer matrix contains macropores with an average diameter of 100 μm throughout the degradation cycle of the polymer. The porous structure permits the migration of cells from the polymer surface to its interior. Cells which become attached in the interior of the polymer have sufficient space to spread.

As shown by the examples, the composites formed of the PLGA were degraded for six weeks in a phosphate buffer (pH 7.4). Material properties characterized during that period included polymer strength and morphology. Cell response in vitro was also examined. The results showed the matrix fabricated by this method to be structurally and mechanically similar to cancellous bone. Prior to degradation, pure polymer specimens exhibited an elastic modulus of 293 MPa and specimens which were 50% HA by weight exhibited a modulus of 1459 MPa. After 6 weeks, the reinforcing effect of ceramic loading had diminished. Modulus of polymer matrices at all HA load levels had decreased sharply to approximately 10 MPa. Mean macro-and micropore diameters of the polymer specimens were 100 μm and 20 μm respectively and remained constant throughout degradation. Microscopy studies illustrated that these macropores were of sufficient size to encourage the migration of plated cells from the surface to the interior of the matrix.

DETAILED DESCRIPTION OF THE INVENTION

Figure 1:
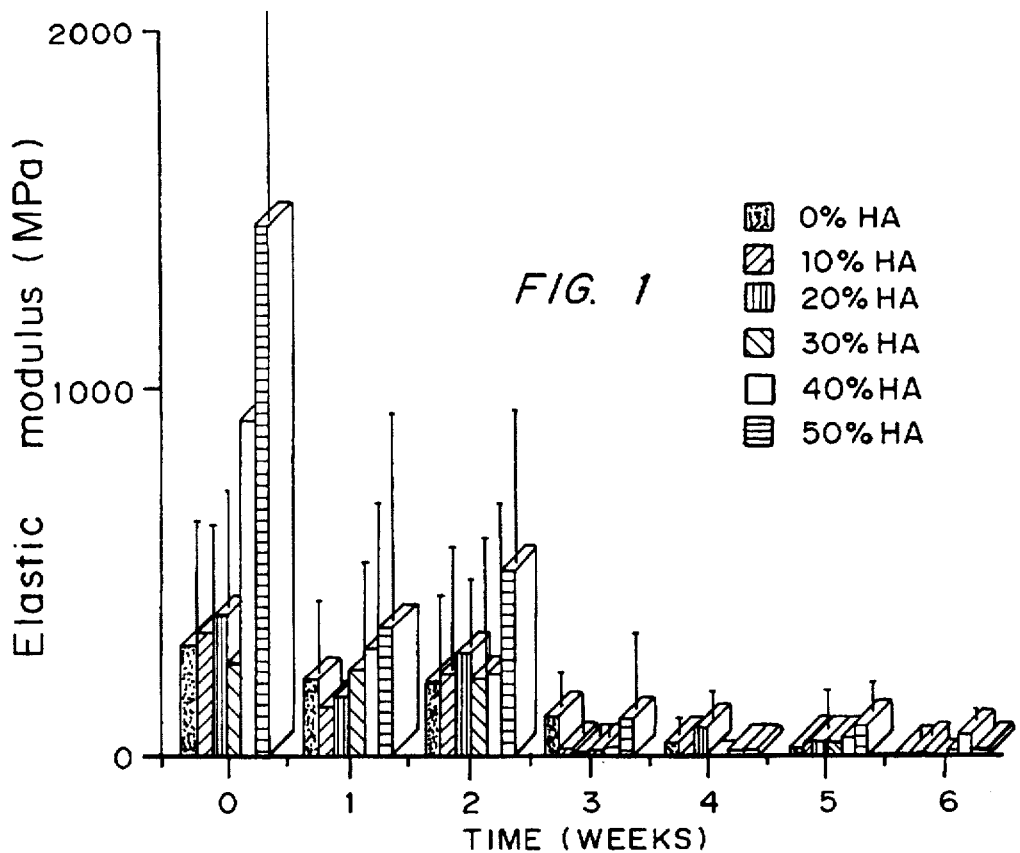
FIG. 1 is a graph of the mechanical strength in compression of HA loaded PLAGA, elastic modulus (MPa) over degradation time (weeks) for 0% HA (dark bar), 10% HA (hatched bar), 20% HA (dotted bar), 30% HA (slashed bar), 40% HA (open bar), and 50% HA (crossed bar).

A biodegradable polymer-ceramic composite was designed for use in bone repair. Other than biocompatability, the critical properties in such an implant include a degree of strength retention over time, and a structural and mechanical equivalence to bone.

Bone repaired with the use of a polymeric implant will be immobilized for between six and eight weeks, the standard procedure for conventional fractures. All fractures are subject to static loading even while immobilized in a cast, i.e., there is a load resulting from the weight of the bone itself. In order for the implant to unite bone segments in a fracture, it must have initial strength sufficient to provide the stability necessary for healing to begin. Further, the resorbing implant must retain a degree of strength throughout the bone remodeling cycle. Strength retention in the implant is governed by the degradation rate of the polymer in the polymer-hydroxyapatite composite described in detail below. Both high strength retention over time and rapid weakening of the scaffold may de detrimental to the bone repair process. Slow implant resorption can shield immature skeletal tissue from the functional stresses necessary for complete remodeling. Conversely, rapid degradation may prematurely shift load bearing to the new bone and cause its collapse.

A preferred biodegradable polymer, a 50:50 polylactide/glycolide copolymer (PLAGA), has poor long-term strength retention. Consequently, an implant constructed of this material alone may allow immature tissue to be overloaded and destroyed. To maintain the integrity of the implant as degradation proceeds, hydroxyapatite (HA) is added to the polymer matrix. Since HA is relatively insoluble in aqueous environments, it continues to lend stability while the polymer hydrolyses. In addition, the ability of HA to bond to bone stabilizes the fixation of the implant in vivo. A strong bone-implant interface helps prevent stress concentration, which could result from an imperfect press fit of the implant. Local bone resorption and motion of the implant could result if stresses are concentrated at the implant interface.

The growth and spread of osteoblasts through a scaffold depend on the number and size of the channels which the cells can penetrate. Porosity promotes the revascularization of tissue. For this reason a graft structurally similar to cancellous rather than cortical bone is desirable because higher levels of porosity permit more rapid graft incorporation. Pores aid in the polymer resorption-cell incorporation cycle by (1) increasing the polymer surface area exposed to the media which degrades it, (2) increasing the surface are for cell attachment, and (3) increasing the pathways by which nutrients can reach the cells. Porous calcium phosphate studies reviewed by Friedlaender and Goldberg 1991 and Jarcho 1981 have established 100 µm as the minimum pore diameter for the successful ingrowth of bone into a matrix.

The design and manufacture of the polymerhydroxyapatite composite implant is described in more detail below.
Selection of Polymers A variety of biocompatible, biodegradable polymers can be used. Typically, these will either be surface erodible polymers such as polyanhydrides or bulk erodible polymers such as polyorthoesters. Other polymers that can be used include polyphosphazenes. In the preferred embodiment, polyhydroxy acids such as polylactic acid (PLA), polyglycolic acid (PGA), and copolymers thereof (PLAGA) are used. These are among the synthetic polymers approved for human clinical use. They are presently utilized as surgical suture materials and in controlled release devices, as well as in other medical and pharmaceutical applications. They are biocompatible and their degradation products are low molecular weight compounds, such as lactic acid and glycolic acid, which enter into normal metabolic pathways.

Furthermore, copolymers of poly(lactic-co-glycolic acid) offer the advantage of a large spectrum of degradation rates from a few days to years by simply varying the copolymer ratio of lactic acid to glycolic acid.

The preferred biodegradable polymers are lactic acid polymers such as poly(L-lactic acid) (PLLA), poly(DL-lactic acid) (PLA), and poly(DL-lactic-co-glycolic acid) (PLGA). The co-monomer (lactide:glycolide) ratios of the poly(DL-lactic-co-glycolic acid) are preferably between 100:0 and 50:50. Most preferably, the co-monomer ratios are between 85:15 (PLGA 85:15) and 50:50 (PLGA 50:50). Blends of PLLA with PLGA, preferably PLGA 85:15 and PLGA 50:50, are also used to prepare polymer materials. Other representative polymers include polyorthoesters, and although not preferred for mechanical characteristics, polyanhydrides. The preferred biodegradable polymers are all degraded by hydrolysis.

Methods for using these polymers are well known and they are commercially available from a variety of sources.

In general, the polymers are dissolved in an organic solvent such as methylene chloride or chloroform to mix with a ceramic, as described below. In the particulate leaching method, the polymer is dissolved in a solvent that does not adversely affect the polymer or the salt, most preferably a volatile organic solvent. The relative amount of solvent will have a minimal effect on the structure of the produced materials, but will affect the solvent evaporation time. Preferably, the solvent contains a chlorine molecule, such as the solvents chloroform and methylene chloride. The preferred solvent is chloroform.
Hydroxyapatite The other major component of the implant is hydroxyapatite, or a similar ceramic formed of tricalcium phosphate (TCP) or calcium phosphate (CaPO$_4$).

Calcium hydroxyapatites occur naturally as geological deposits and in normal biological tissues, principally bone, cartilage, enamel, dentin, and cementum of vertebrates and in many sites of pathological calcifications such as blood vessels and skin. Synthetic calcium hydroxyapatite is formed in the laboratory either as pure $Ca_{10}(PO_4)_6(OH)_2$ or hydroxyapatite that is impure, containing other ions such as carbonate, fluoride, chloride for example, or crystals deficient in calcium or crystals in which calcium is partly or completely replaced by other ions such as barium, strontium and lead. Essentially none of the geological and biological apatites are "pure" hydroxyapatite since they contain a variety of other ions and cations and may have different ratios of calcium to phosphorous than the pure synthetic apatites.

In general, the crystals of pure synthetic apatites, geological apatites and many impure synthetically produced apatites are larger and more crystalline than the biological crystals of bone, dentin, cementum and cartilage. The crystals of bone, dentin and cementum are very small, irregularly shaped, very thin plates whose rough average dimensions are approximately 10 to 50 angstroms in thickness, 30 to 150 angstroms in width, and 200 to 600 angstroms in length. This results in their having a very large surface area to present to the extracellular fluids which is important for the rapid exchange of ions with the extracellular fluids. In general, bone contains approximately 35% organic constituents, the major component being collagen fibrils. See, for example, Cohen-Solal, et al., "Identification of organic phosphorus covalently bound to collagen and non-collagenous proteins of chicken-bone matrix: the presence of O-phosphoserine and O-phosphothreonine in non-collagenous proteins, and their absence from phosphorylated collagen" *Biochem. J.* 177:81–98 (1979).

The synthetic materials are highly diverse, as reported in the literature. For example, the characterization of four commercial apatites was reported by Pinholt, et al., *J. Oral Maxillofac. Surg.* 50(8), 859–867 (August 1992); *J. Cariofac. Surg.* 1(3), 154–160 (July 1990) reports on a protein, biodegradable material; Pinholt, et al., *Scand. J. Dent. Res.* 99(2), 154–161 (April 1991) reports on the use of a bovine bone material called Bio-Oss™; Friedman, et al., *Arch. Otolaryngol. Head Neck Sura.* 117(4), 386–389 (April 1991) and Costantino, et al., *Arch. Otolaryngol. Head Neck Surg.* 117(4), 379–384 (April 1991) report on a hydroxyapatite cement; Roesgen, *Unfallchirurgle* 16(5), 258–265 (October 1990), reports on the use of calcium phosphate ceramics in combination with autogenic bone; Ono, et al., *Biomaterials* 11(4), 265–271 (May 1990) reports on the use of apatite-wollastonite containing glass ceramic granules, hydroxyapatite granules, and alumina granules; Passuti, et al., *Clin. Orthop.* 248, 169–176 (Nov. 1989) reports on macroporous calcium phosphate ceramic performance; Harada, *Shikwa-Gakuho* 89(2), 263–297 (1989) reports on the use of a mixture of hydroxyapatite particles and tricalcium phosphate powder for bone implantation; Ohgushi, et al., *Acta Orthop. Scand.* 60(3), 334–339 (1989) reports on the use of porous calcium phosphate ceramics alone and in combination with bone marrow cells; Pochon, et al., *Z-Kinderchir.* 41(3), 171–173 (1986) reports on the use of beta-tricalcium phosphate for implantation; and Glowacki, et al., *Clin. Plast. Surg.* 12(2), 233–241 (1985), reports on the use of demineralized bone implants.

As used herein, all of these materials are generally referred to as "hydroxyapatite". In the preferred form, the hydroxyapatite is particles having a diameter between approximately ten and 100 microns in diameter, most preferably about 50μ in diameter.

Method of Making Polymer-Hydroxyapatite Composite

The polymer-hydroxyapatite composite must be made using a method yielding a porous structure having defined mechanical properties. In the preferred embodiment, a particulate leaching technique is used which is a modification of the method of Mikos, et al. *Biomaterials* (1992). While the prior art methods were an effective means to create macropores in disks, they were less successful in creating pores in thicker polymeric structures, as salt sedimented if the polymer solution was not viscous enough to hold it in suspension. A high viscosity polymer solution obtained by emulsification which prevented sedimentation of the salt was used to overcome this latter problem. Incorporation of particulate hydroxyapatite was used to increase the strength and osteoconductive potential of the polymer matrix.

Mixing of Polymer and Particulates

The polymer solution is mixed with the hydroxyapatite particles and inert particles to be removed by leaching. The order of addition is typically not critical, i.e., the polymer can be mixed with hydroxyapatite, then leachable particles added, or vice versa. For ease of reference below, "polymer" refers either to the polymer solution prior to addition of hydroxyapatite, as well as to the polymer solution containing the hydroxyapatite particles.

In the method that was ultimately determined to be useful in making relatively thick implants, rather than membranes or films as produced using previously described salt-leaching polymer casting methods, a number of modifications were required. These dealt primarily with altering the ability of the polymer solution to hold the particulate material in suspension. It was ultimately determined that the most reproducible and efficient manner in which this could be accomplished was to increase the viscosity of the polymer. Techniques to increase the polymer viscosity include (1) to use less solvent to dissolve the polymer, i.e., to increase the polymer concentration in the polymer solution, (2) to heat the solution past $T_g$ of the polymer, for example, for PLAGA $T_g$ is 45° C., (3) to use a non-solvent to precipitate a thick, sticky mass from the polymer solution, as described by Hollinger, and preferably (4) to create an emulsion of the polymer either mechanically or chemically. Although Voids are created in all of the resulting polymer matrices using the first three methods, they do not always permeate the material, nor is their size or distribution even.

A foam can be created by mechanically pumping air into a fluid sample rather than by using chemical means. When a vacuum is applied to a container holding a viscous liquid sample, the volume of the sample rises. A solid, porous material can be obtaining by freezing with liquid nitrogen to trap the air bubbles (which are fairly evenly distributed), and removing solvents by vacuum. The vacuum can be controlled with a three-way valve and a solvent trap and filters will prevent flow of the solvent into the motor/pump, as shown schematically below.

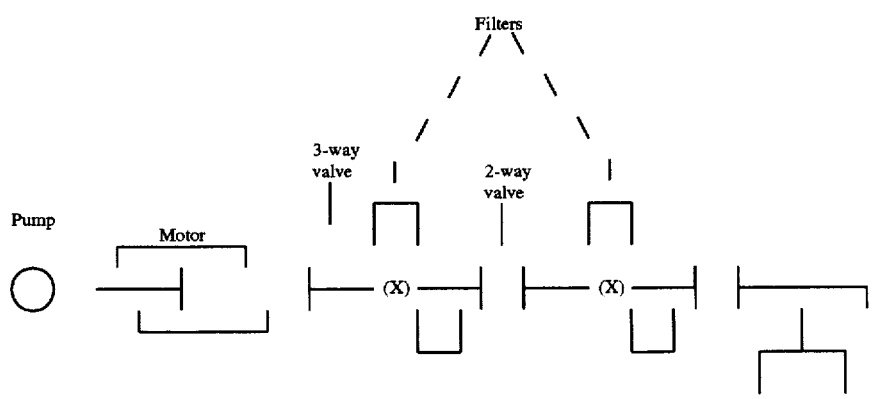

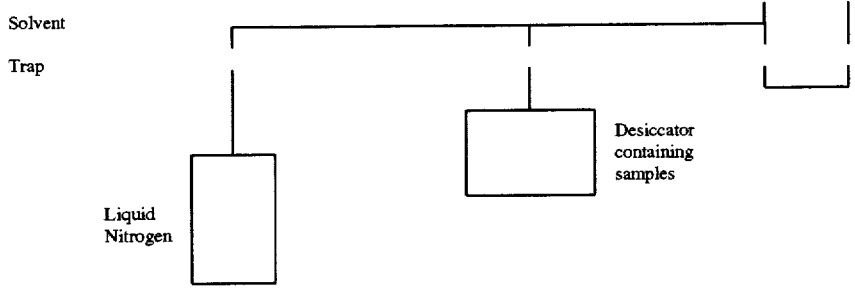

An emulsion is the result of the combination of two immiscible liquids such that one phase is uniformly dispersed in other. The bulk phase surrounds droplets of the dispersed phase. Emulsions are generally unstable since their creation increases the surface free energy of the system as droplets form. This thermodynamic instability leads to a growth in the size of droplets as the system moves toward a lower energy state and a complete separation of the two phases. An emulsifying agent can be used to lower surface tension by forming an interfacial film between droplets and the bulk phase, thereby preventing coalescence of the dispersed droplets. The emulsifier can also increase viscosity of the emulsion, as described by Osol, Arthus (editor), Remington's Pharmaceutical Sciences, Easton: Mack Publishing, 310–17, 1246–51, 1453–4 (1980).

The type of emulsion formed, oil in water (O/W) or water in oil (W/O), depends on the relative rates of coalescence of the droplets of each phase. Choice of emulsifying agent affects the type of emulsion formed. Hydrophilic emulsifiers lead to the formation of O/W emulsions, and lipophilic (hydrophobic) emulsifiers lead to W/O emulsions. A numerical scale, the hydrophilic-lipophilic balance (HLB) scale, quantifies these characteristics of the emulsifying agent. Surfactants with HLB number 1–10 are lipophilic, and those with number over 10 are hydrophilic.

Formation of W/O emulsions could trap droplets of water in a polymer solution which could later be removed by vacuum. Remington's 1980 lists several surfactants capable of forming W/O emulsions. Examples of lipophilic emulsifiers include polyoxyethylene sorbitan monooleate (Tween™80), a syrup highly soluble in both water and methanol, and bentonite, a hydrated colloidal clay which may form highly viscous suspensions and gels, (available from Sigma Chemical Co.), although their use is not preferred.

In the preferred embodiment, a 40% w/v solution of PLAGA in chloroform was used to suspend particulate hydroxyapatite (HA) and NaCl crystals (100–250 μm in diameter). The w/w ratio of polymer to salt was 1:1, and the ratio of polymer to ceramic ranged from 1:0 to 1:1. To this suspension a 1% aqueous solution of poly(vinyl alcohol) (PVA), mw 25,000, was added with a ratio of chloroform to PVA solution of 7:3, to form an emulsion.

The selection of the polymer and hydroxyapatite are described above.

The particles can be any salt that forms crystals or particles having a diameter less than 250 microns, which is easily removed from and does not react with the polymer, and is non-toxic if some residue remains in the polymer after leaching. Examples other than salts are proteins such as gelatin and agarose, starches, polysaccharides such as alginate and other polymers. Preferably, the salt is a sodium salt, such as sodium chloride, sodium tartrate and sodium citrate, and other water soluble salts or compounds not soluble in the polymer solvent, for example, chloroform or methylene chloride. The most preferred salt is sodium chloride.

If the particulate matter can be leached by a fluid other than water, the risk of erosion damage to hydrolytically unstable polymers such as PLAGA can be reduced. This requires using a substance soluble in a non-solvent for the polymer, in the case of PLAGA, methanol or ethanol, but not in a solvent capable of dissolving or degrading the polymer.

Preferably, the particles are first sieved through a mesh or a series of screens to provide particles of relatively uniform diameter. The diameter of the particles is between 100 and 250 microns.

The particles are added to a polymer solution preferably in the ratio of particles to polymer of between 0.1:1 and 1:1, most preferably 1:1, where the polymer can contain between 1:0.1 and 1:1, most preferably between 10 and 50% by weight of HA. The initial salt weight fraction is instrumental in determining the characteristics of the composite material.

Although not preferred, it is possible to add binders of the type added to commercial hydroxyapatite preparations to provide additional stability.

Shaping of the Materials

The polymer solution can be cast into any appropriate mold, with the dried polymer material retaining the shape of the mold. The solvent is evaporated from the salt and polymer mixture over a period of time, preferably forty-eight hours, at room temperature. Any residual solvent is subsequently removed by lyophilization. The resulting mixture will be in the form of a polymer material interspersed with particles.

Material Crystallinity

The mixture can be heated after removal of the solvent to decrease or increase the crystallinity of the material. Alternatively, particles can be directly dissolved out of the material in the absence of heat to prepare materials having a high crystallinity. Materials having high crystallinity, i.e., greater than 20%, will be stronger and will therefore degrade slower than materials having reduced crystallinity.

To obtain materials with a lower crystallinity and a faster rate of degradation after implantation, the salt and polymer mixture is heated at a temperature that will melt the polymer without affecting the particles. Preferably, the mixture is heated at a temperature between 15° and 20° C. higher than the melting temperature ($T_m$) of the polymer. A temperature approximately 15° C. higher than the polymer melting temperature is most preferred. The mixture is heated for a sufficient amount of time to uniformly melt the polymer. One hour is normally sufficient.

The melted polymer is cooled to room temperature at a predetermined constant rate. The rate of cooling will also affect crystallinity and the rate of biodegradation after implantation. A faster cooling rate will produce a material having a lower degree of crystallinity. Preferably, the mixture is cooled at a rate between 5° and 20° C. per minute. The preferred cooling rate for the formation of a material for use in liver or cartilage cell transplants is large enough to yield amorphous PLLA materials. The mixture cooled at the predetermined rate will have the desired degree of crystallinity for the intended use.

Particle leaching

The resulting crystallized polymer and particle composite material is immersed in a liquid in which the particle is soluble for a sufficient amount of time to allow leaching of substantially all of the particle, but which does not dissolve or detrimentally alter the polymer. The preferred liquid is water, most preferably distilled-deionized water, which does not dissolve the polymer nor cause measurable hydrolysis of the polymer within the time required for processing. Preferably, the particle is leached out of the material in a vessel containing distilled-deionized water for a period of forty-eight hours for a polymer such as PLLA or ninety-six hours for PLGA, and the water is changed approximately every twelve hours. The vessel can be placed in a heated waterbath or incubator and shaken to enhance particle leaching. Most preferably, the vessel of water is placed in a waterbath heated to approximately 37° C. and is shaken at approximately 100 rpm to enhance the leaching process.

Removal of the particles will create a polymer material having a plurality of relatively evenly spaced interconnected interstitial spaces or pores, formerly occupied by the particle crystals, into which cells can migrate, attach, and proliferate to create an organ or appendage. The porosity of the material is very high, greater than 90%.

The polymer material is dried for a sufficient amount of time to remove any water that may be occupying the pores. Preferably, the polymer material is air-dried for approximately twenty-four hours followed by vacuum-drying with a lyophilizer for approximately forty-eight hours.

Incorporation of other Materials

The composite material can be used not only in the repair and replacement of bone but also in drug delivery, to bone or as a part of the repair process. Examples of materials which can be incorporated include antibiotics, chemotherapeutics and bone cell inducers and stimulators, including the general class of cytokines such as the TGF-β superfamily of bone growth factors (Cytokines and Bone Metabolism, Gowen, ed (CRC press, 1992), (available from Boehringer-Mannheim), the family of bone morphogenetic proteins, osteoinductors, and/or bone marrow or bone forming precursor cells, isolated using standard techniques.

With reference to sources and amounts of various materials that can be included see, for example, Glowacki, J., et al. "The role of osteocalcin in osteoclast differentiation" *J. Cellular Biochem.* 45:292–302 (1991); Ballock, T. T., et al. "Regulation of collagen expression in periosteal cells by three members of the TGF-B superfamily" *Thirty Ninth Annual Meeting, Orthopaedic Research Society;* 18,734 (1993); Ripamonti, U., et al. "Induction of bone in composites of osteogenin and porous hydroxyapatite in baboons" *J. Plastic and Reconstructive Surg.* 89:731– 739 (1991); Ripamonti, U., et al. "Growth and morphogenetic factors in bone induction: role of osteogenin and related bone morphogenetic proteins" *CRC Critical Reviews in Oral Biol. Med.* 3:1–14 (1992); Ripamonti, U., et al. "Initiation of bone regeneration in baboons by osteogenin, a bone morphogenetic protein" *Matrix;* 12:40–55 (1992); Ripamonti, U., et al. "Xenogeneic osteogenin and demineralized bone matrices including human induced bone differentiation in athymic rats and baboons" *Matrix* 11:404–411 (1991); Cook, S. D., et al. "Restoration or large diaphyseal segmental defects in rabbits using recombinant human osteogenic protein (OP-1)" *Combined meetings of Orthopaedic Research societies of USA, Japan and Canada* 1, 66 (1991); Miyamoto, S., et al. "Trans-filter bone induction in monkeys by bone morphogenetic protein" *Thirty Ninth Annual Meeting, Orthopaedic Research Society* 18, 99 (1993); Yasko, A. W., et al. "Comparison of recombinant human BMP-2 versus cancellous bone to heal segmental bone defects" *Thirty Ninth Annual Meeting, Orthopaedic Research Society* 18, 100 (1993); Aspenberg, P., et al. "Bone morphogenetic protein induces bone in the squirrel monkey, but bone matrix does not" *Thirty Ninth Annual Meeting, Orthopaedic Research Society* 18, 101 (1993); Iwasaki, M., et al. "Bone morphogenetic protein-2 stimulatesin high denis in high density culture of periosteum-derived cells" *Thirty Ninth Annual Meeting, Orthopaedic Research Society* 18, 483 (1993); Cook, S. D., et al. "Recombinant human osteogenic protein-1 (rhOP-1) heals segmental long-bone defects in non-human primates" *Thirty Ninth Annual Meeting, Orthopaedic Research Society* 18, 484 (1993); and Hunt, T. R., et al. "Healing of a segmental defect in the rat femur using a bone inducing agent (BIA) derived from a cultured human osteosarcoma cell line (SAOS-2)" *Thirty Ninth Annual Meeting, Orthopaedic Research Society* 18, 489 (1993).

Implantation of the Matrix

The matrix described here is implanted using standard surgical techniques for repair or replacement of bone. The matrix can be directly implanted into the site where bone growth is desired, or seeded with appropriate cells such as osteoblasts or osteoblast-like cells and then implanted. In the preferred embodiment, the matrix will be pre-cast into a desired shape for repair of the bone in need of treatment thereof.

EXAMPLES

In the following examples, NaCl was dispersed in a polymer solution and removed by leaching after the cast had solidified. Pore size could be controlled by changing the diameter of the grains of salt. The resulting matrix is an aggregate of polymeric microspheres, and the porosity results from the combined effects of imperfect packing of the spheres and a salt leaching process. The level of porosity and pore size help simulate the proper environment for cell adhesion and growth. The incorporation of particulate HA to the matrix lends strength to the implant as the polymer degrades. Further, since the matrix includes microspheres, the system has potential for use as a vehicle for drug delivery. The effects of ceramic loading and macroporosity on the mechanical properties of the implants, and the effects of degradation of the implants in vitro were investigated. Both mechanical strength and weight loss were monitored. Changes in implant morphology as degradation occurred were quantitatively assessed using mercury porosimetry and were documented using scanning electron microscopy. Finally, the viability of the polymer matrix as a system for cell attachment in vitro was investigated.

Example 1

Preparation of Polymer-Hydroxyapatite Composites
Materials and Methods

A 50:50 polylactide/glycolide copolymer (PLAGA, [DuPont Medisorb, lot S2127 S144], and unfired particulate HA (lot HAG 89272B, Howmedica), were used in the fabrication of polymer matrices. Six types of macroporous polymer plugs were prepared for testing at ceramic (weight) loads 0, 10, 20, 30, 40 and 50% HA.

Polymer Processing Techniques

The assumption underlying this technique was that a stable water in oil emulsion could be created and that the trapped droplets could be driven off by vacuum. Voids left in the polymer structure after sublimation of water would be pores. The results is a porous three dimensional matrix composed of polymeric microspheres.

Polymer films were fabricated by this technique, and microscope examination revealed that these films were formed of clumps of microspheres of varying sizes stuck to each other. Small channels ran through films due to the imperfect packaging of the spheres. Films were immersed in water at 37° C. and agitated to see if spheres would disperse. After 10 days in water, the spheres did not disperse, indicating that the system would remain stable even when partial degradation had occurred.

NaCl was incorporated into the process to open the channels between the spheres. Microscope examination of the resulting films revealed interconnected spaces permeating the matrix. The procedure was subsequently modified to make the polymer solution more viscous. Finally, the polymer was cast into a mold to produce a hard, white cylindrical structure visibly similar to bone.

To describe the technique briefly, a 40% w/v solution of PLAGA in chloroform was used to suspend particulate hydroxyapatite (HA) and NaCl crystals (100–250 μm in diameter). The w/w ratio of polymer to salt was 1:1, and the ratio of polymer to ceramic ranged from 1:0 to 1:1. To this suspension a 1% aqueous solution of poly(vinyl alcohol) (PVA) [Polysciences, Inc., 88% mole hydrolyzed, mw 25,000, lot #413322] was added with a ratio of chloroform to PVA solution of 7:3. The resulting emulsion was cast into a cylindrical mold, air dried for 48 h and vacuum dried for an additional 48 h. At this point, the polymer was demolded and the salt leached by immersion in deionized water at 37° C. for 48° h with one change in immersion medium after 24 h. Upon removal from the bath, polymer was air dried for 48 h, then vacuum dried for an additional 48 h.

The steps involved in fabricating these matrices are the same for each HA load, while the quantities of the ingredients change. First, weigh equal amounts of polymer and salt and place in a scintillation vial. Diameters of NaCl particles should range between 100 and 250 μm. This step should ensure uniform pore diameter and 50% porosity of samples. Next, add hydroxyapatite in percentage proportion to polymer weight. Dissolve polymer and suspend other dry ingredients in chloroform. After dissolution has occurred, add PVA solution and hand shake until viscosity noticeably increases. Pour into mold. Let samples solidify 1–2 days under hood, then lyophilize for 2 days. Demold, then leach salt by immersing samples in deionized water for 2 days at 37° C. Change the water after 24 h. Set under the hood for a few hours, freeze and lyophilize for 2 days. At the end of this process samples are ready for testing.

Compositions that were prepared:

| | |
|---|---|
| A. | 0% HA |
| | 1.5 g PLAGA, 1.5 g NaCl |
| | 3.75 ml chloroform |
| | 1.6 ml of 1% PVA solution. |
| B. | 10% HA |
| | 1.45 g PLAGA, 1.45 NaCl, .16 g HA |
| | 3.625 ml chloroform |
| | 1.55 ml PVA solution. |
| C. | 20% HA |
| | 1.4 g PLAGA, 1.4 g NaCl, .35 g HA |
| | 3.5 ml chloroform |
| | 1.5 ml PVA solution. |
| D. | 30% HA |
| | 1.3 g PLAGA, 1.3 g NaCl, .56 g HA |
| | 3.25 ml chloroform |
| | 1.4 ml PVA solution. |
| E. | 40% HA |
| | 1.0 g PLAGA, 1.0 g NaCl, .67 g HA |
| | 2.5 ml chloroform |
| | 1.0 ml PVA. |
| F. | 50% HA |
| | 1.0 g PLAGA, 1.0 g NaCl, 1.0 g HA |
| | 2.5 ml chloroform |
| | 1.0 ml PVA solution. |

Example 2

Polymer-Hydroxyapatite Composite Characterization

Properties of the polymer matrices fabricated by the method described in Example 1 were characterized through a degradation cycle of the polymer. In a six week study, polymer samples of each type were degraded in a phosphate buffer (pH 7.4) at 37° C. At three time points: two, four and six weeks, samples were removed from the media and weight loss and porosity were determined. Visible changes in morphology were assessed at the beginning and end of the study. Mechanical strength in compression was tested weekly for several samples at each ceramic load level.

Compression Testing

Cylinders were prepared with a diameter to height ratio of approximately 1:1. At time 0 and thereafter at one week intervals for six weeks, three to five cylinders at each HA load were removed from the media and subject to mechanical testing. Samples were measured (height and diameter) and tested wet in compression on an Instron machine [Model 4201] at a constant crosshead rate of 0.5 mm/min. Data were collected by computer and analyzed to determine elastic modulus and yield of a sample. Average and standard deviation for each set of plugs was calculated. For each of the 6 sample types mean modulus and compressive yield strength were plotted versus time.

Four pure PLAGA (0% HA) macroporous samples were tested in compression on an Instron. Moduli of these first generation samples were 51, 60, 133 and 350 MPa. The wide range of strengths indicated that the samples were of inconsistent pore size and/or distribution. The strength was acceptable, and HA had yet to be incorporated into polymer matrix. The polymer processing technique needed adjustment to ensure a more even distribution of pores, and the problem was resolved by increasing the viscosity of the solution.

The modified method increased the polymer to solvent ratio from 0.2 g PLAGA/ml chloroform to 0.4 g PLAGA/ml chloroform. The viscosity of the polymer solution noticeably increased and the salt did not sediment as quickly as it had previously, though some degree of sedimentation did occur.

Mechanical properties of the polymer samples were assessed in terms of elastic modulus and compressive yield strength. FIG. 1 shows the average modulus of elasticity of each sample population at six time points. At 0 weeks degradation, Young's Modulus of the polymer was a function of ceramic content. Increased HA loading resulted in increased modulus. The variation in the 30% samples was not statistically significant ($p>0.1$). The pre-degradation modulus of 50% HA was 1459 MPa, and that of 0% HA was 293 MPa. Moduli of 40% and 50% HA samples were significantly higher than those for samples at lower ceramic loads ($p<0.01$).

After one week degradation in buffer, the moduli ranged from a low of 117 MPa at a 10% HA load to a high of 340 MPa at a 50% HA load. Samples of high ceramic content (30, 40 and 50% HA) were significantly stronger than those of lower HA loads ($p<0.05$). Two weeks' degradation again showed 50% HA to be significantly stronger than the other samples ($p<0.01$). However, by three weeks, the strengthening effect of ceramic loading was no longer apparent. From this point to the end of the study, all moduli within a time point were approximately equal. Across time points, they varied within a limited range of between one and 100 MPa.

Figure 2:
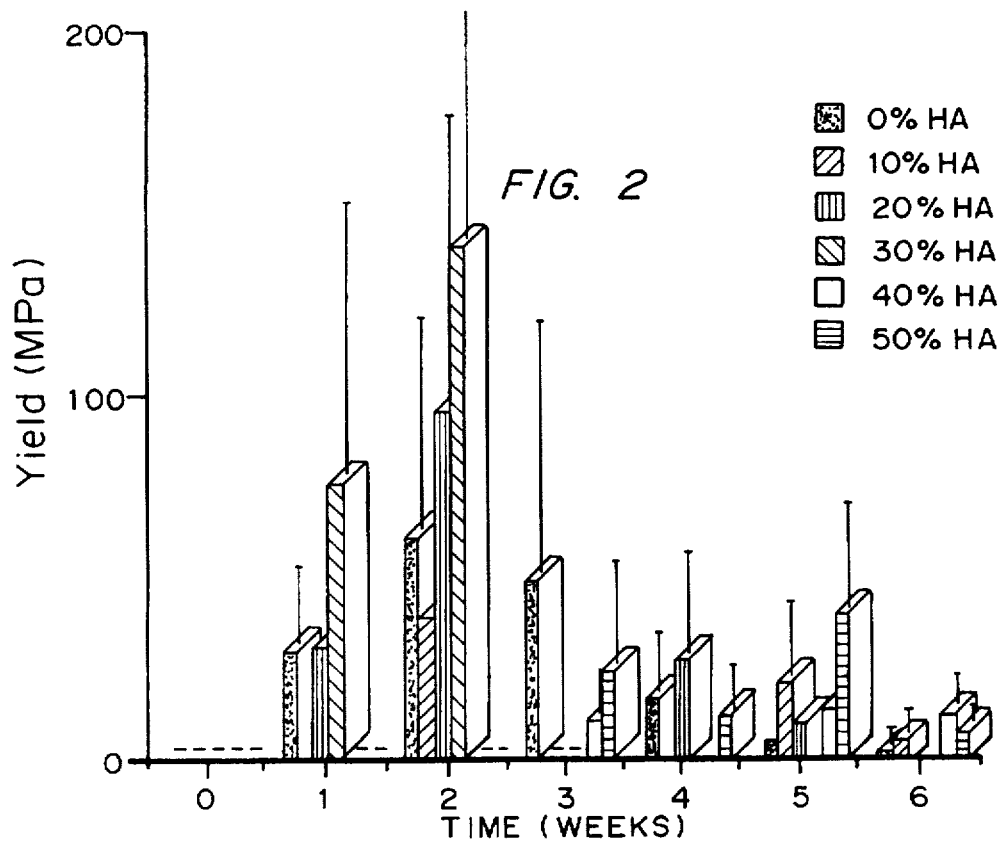
FIG. 2 is a graph of the compressive yield of HA loaded PLAGA, yield (MPa) over degradation time (weeks), 0% HA (dark bar), 10% HA (hatched bar), 20% HA (dotted bar), 30% HA (slashed bar), 40% HA (open bar), and 50% HA (crossed bar).

FIG. 2 presents the stresses at which yield occurred in samples under compressive loading. The dashes above the x-axis of the plot (-) indicate that samples did not yield at the maximum stress to which they were subject. For the first three time points, resistance to yield was related to increased HA content. At time zero, no samples failed under stresses between 100 and 350 MPa. At time 1 week, the 0, 20, 30% HA samples yielded under 28, 30 and 75 MPa respectively. The 30% samples exhibited a significantly higher yield than the other two groups ($p<0.05$). After 2 weeks, all but the 40 and 50% ceramic samples yielded below a load of 150 MPa. Of the samples which did yield at this time, the 30% HA failed at a stress significantly higher than those at which the others failed ($p<0.01$). The maximum stress on 40 and 50% samples was 150 MPa, but this load did not lead to failure.

After 3 weeks time, the presence of HA had little effect in preventing yield. Yield stresses of the polymer in advanced stages of degradation were 10–30 MPa.

A few general statements may be made about the patterns of mechanical behavior of the polymer when subject to loading. First, the elastic modulus of the samples decreased as degradation proceeded. Second, modulus increased as ceramic content was increased. A third interesting trend was the rapid deterioration of strength of 50% HA over time relative to the deterioration of pure PLAGA samples.

Mechanical tests showed that through the first five weeks of the degradation cycle the elastic moduli of the polymer of all HA loads fell safely within the range of moduli of cancellous bone identified by Keaveny and Hayes. At 6 weeks' degradation, however, all moduli had sharply decreased to values near or below 10 MPa, the lower bound for modulus of cancellous bone as defined by Keaveny and Hayes. Prior to degradation, samples at 40 and 50% HA loads exhibited moduli 3–5 times higher than those at lower ceramic load levels. Although HA has significant strengthening effect prior to and in the early stages of polymer degradation, its role diminishes as erosion of the polymer proceeds. Since HA is chemically inert, it cannot become bound to the polymer, only suspended in the matrix. In the early stages of polymer degradation the high levels of chain linkage hold the particles of HA in place. As the polymer chains become cleaved, the loose HA particles are not strong enough to preserve the integrity of the matrix. This could explain the vast differences in the elastic moduli of samples of high and low HA levels prior to degradation but not during the advanced stages of degradation.

The trend in the first two weeks of the yield study indicated that higher HA loads prevented yield, or at least increased the stress level required to produce failure in the samples. During this period, yield of the material at a level comparable to that at which cancellous bone yields. After two weeks, yield stresses in the polymer decrease to between 10 and 30 MPa. In addition, at between three and six weeks' degradation there is no apparent connection between HA load and yield stress.

Weight Loss in Deionized Water

Empty glass scintillation vials were weighed and labeled to identify their contents. The label indicated ceramic load level, sample number, and time to be removed from the immersion medium. After weights of the samples were recorded, each sample was placed in its respective vial, and 20 ml phosphate buffered saline (pH 7.4) was added. Samples were capped and placed in an incubator at 37° C.

Six time points were chosen at one week intervals. At each time point up to six weeks, liquid from the vials was removed and replaced with 20 ml of fresh buffer. At two, four and six weeks, three vials containing a polymer plug of a particular sample type were removed and dried to constant weight. Total weight loss, percentage loss, average and standard deviation for each triplet was calculated.

After 2 weeks' degradation, samples had lost roughly 10% of their weight. By the end of 6 weeks immersion in buffer, weight loss ranged between 30 and 50% of the pre-degradation weight of the samples. Student's t-test showed the increase in weight loss between 2 and 6 weeks' degradation to be statistically significant for most HA load levels ($p<0.05$).

Samples at HA loads less than 40% lost the most weight over the 6 week degradation period. The 40 and 50% HA samples lost at most 20% of their original weight, while the others lost up to 50% of their original weight. At advanced states of polymer degradation (4–6 weeks), there was a trend indicating lower total weight loss with increased ceramic content.

These experiments showed a general increase in weight loss as time passed. There was no visible reduction of sample volume during degradation.

In samples of 40–50% HA content, the maximum amount of weight lost was approximately 20%. Assuming no loss of HA, 35–40% of the polymer in these samples was degraded away. This is comparable to the amount of polymer degraded in the other samples. Pure polymer samples were degraded by 33% during the six week period of immersion in buffer, and samples of 10, 20 and 30% HA lost 30–40% of their polymer content to degradation. HA had no effect in slowing polymer degradation.

Mercury Porosimetry

Porosity of samples was tested at 0, two, four and six weeks degradation to quantitatively assess changes in sample morphology. Samples used in weight loss studies were subject to testing on a mercury porosimeter [Micromeritics Pore Sizer 9320]. Samples were sealed in penetrometers and secured into the ports on the machine. The penetrometers were evacuated to between 0.5 to 0.8 psia and data were recorded by computer as mercury was pumped into the samples. Mercury intrusion pressures reached a maximum of 15 psia. Experiments were conducted to find mean micro-and macropore diameter.

Figure 3:
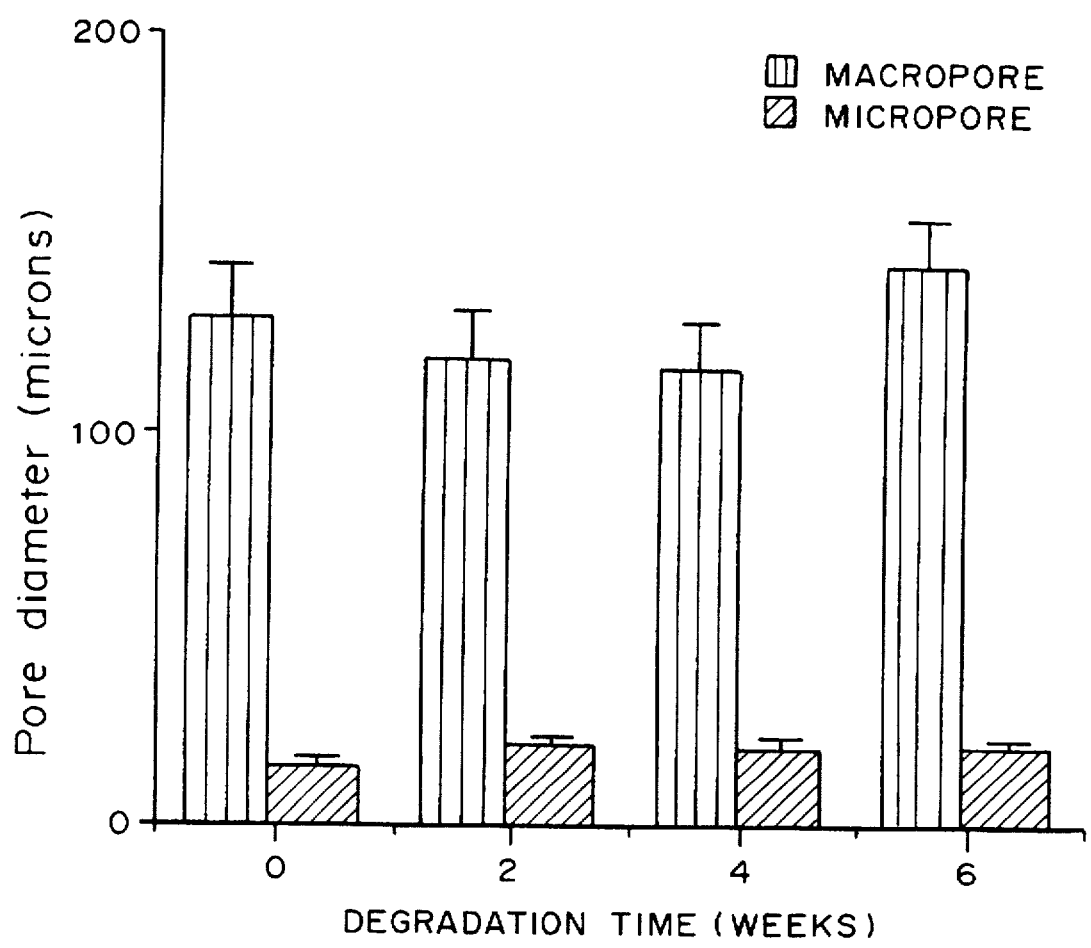
FIG. 3 is a graph of the average macro-and micropore diameter during polymer degradation, pore diameter (microns) over degradation time (weeks) for macropore (dark bar) versus micropore (hatched bar).

Mercury pumped into the polymer at low pressured (0.5–0.8 psia) uncovered the largest pores in the sample, while high pressure mercury intrusion (14–15 psia) detected smaller pores. HA loading had no effect on pore size. FIG. 3 presents mean macro-and micropore diameters through the degradation cycle of the polymer. Both mean macro-and micropore size remained constant over the six week period. Average macroporosity fell in the range of 110–150 μm and microporosity between 18 and 20 μm.

Maximum pore size as a function of time was also determined in this study. Over the six week degradation period, the maximum pore size in the polymer matrices ranged from 300 to 500 μm. The mean macropore size in the polymer remained in the range 110–150 μm throughout degradation. This indicates that the PLAGA matrix should be able to support cell growth.

The largest pores determined by porosimetry prior to degradation of the polymer were 350 μm in diameter. Studies showed, as expected, that pores became larger as degradation of the polymer proceeded. It is interesting to note that at time zero some pores were larger than the grains of salt used to create them. Since the mean pore diameter in the polymer was within the range of sizes of the salt particles used in polymer fabrication, pores were the result of salt leaching. A possible explanation for the presence of oversized pores is that they were the result of the emulsion process.

Environmental Scanning Electron Microscopy (ESEM)

At time 0, three and six weeks, samples were dried and examined with an environmental scanning electron microscope [ElectroScan ESEM] to document general morphological changes through the degradation cycle. Both radial and longitudinal cuts were made in cylindrical samples in order to inspect the surface and interior of the polymer. Photographs were taken at two different magnification levels—100×for imaging the surface and interior of the polymer and 300×to visualize the interior of a pore.

Samples manufactured using 0.4 g/ml chloroform and particulate hydroxyapatite was incorporated into the solution. Environmental scanning electron microscopy revealed an irregular surface, as well as irregular pore size and distribution. Magnification of a pore seen on an end cut showed that the pore itself was elliptical, approximately 100 μm in one direction and 200 μm in the other. Micropores were also clearly apparent in the polymer. An irregular polymer surface was the result of the presence of microspheres of distorted shapes and uneven sizes. Although microspheres were present, the system was not entirely composed of these spheres.

Analysis of a sample which had been cut longitudinally illustrated that there were pores throughout the polymer matrix and the directionality of these pores was random. The interior of the matrix had a considerable amount of void space. The largest of these voids was 400 μm in breadth. Smaller pores ranged in size from 25 to 200 μm.

Further analysis of another photograph shows that the surface appears smooth and three macropores roughly circular in shape are visible. The diameters of these pores are approximately 250, 300 and 400 μm. Within these pores are smaller pores, which appear as the darkest regions on the photograph. This suggests that there was a degree of interconnectivity of the pores through the matrix. A photograph of the interior of a pure PLAGA sample which had been cut longitudinally before it was examined under the microscope shows a single pore running the length of the picture, widening from a diameter of 200 μm to about 500 μm. The photograph represents a 1 mm section of a polymer sample which had an original overall length of about 10 mm. The wall of the pore has an irregular surface which could provide sites for cell attachment.

Analysis of the top surface of a 50% HA sample which had not undergone degradation in media showed two grains of salt which were not leached during fabrication of the polymer were nested in pores 100 μm in diameter. Larger, irregularly shaped pores were found above and to the left. These pores spanned 200 μm. The surface of this polymer appears rough in comparison to the surface of pure PLAGA. Bright white particles scattered over the surface of the polymer dominated this photograph. These are grains of HA.

Analysis of a 0% HA sample which had been immersed in buffer for six weeks showed that the matrix had degraded to the point where it was no longer a continuous structure. In fact, the sample had crumbled during freeze drying and was reduced to a mass of powder. These loose particles ranged in size from 50 to several hundred microns. Micropores in the grains of polymer are visible due to the high magnification level of the photograph (270×). Diameters of these micropores were less than 25 μm.

Analysis of the surface of a 50% HA sample after 6 weeks' degradation showed that the surface appeared white and granular. The sample was composed primarily of particulate hydroxyapatite, as much of the polymer has been degraded during the 6 week immersion period. Pores were highly interconnected and irregularly shaped. Degradation of the polymer enlarged the pores, as porosimetry studies showed. Diameters of these pores were approximately 200 μm.

SEM confirmed that the polymer matrix contained pores, many of which were approximately 100 μm in diameter. Microscopic examination of the polymer showed the pores to be interconnected. Contours of the interior of several pores visualized by SEM indicated that the interior of the polymer could provide suitable sites for cell attachment.

Microspheres were evident in the matrices, but they appeared distorted. Furthermore, SEM pictures illustrated the complete physical deterioration of the 0% HA matrix at 6 weeks' degradation and the relative stability of the 50% HA matrix. This serves as strong evidence that the polymer must have some level of reinforcement if the implant is to be used in load-bearing applications.

Example 3

Cell Adhesion of Polymer-Hydroxyapatite Composites

Adhesion of MC-3T3 cells to polymer samples was investigated over a 24 h period. Confocal laser microscopy and cell count were used to determine the degree of cell attachment. The goal of this study was to determine whether cells would attach to the surface of the polymer and whether they would migrate into the matrix through the pores in the material.

Cells were plated on 0 and 50% HA polymer samples and tissue culture polystyrene (TCPS) at low density and incubated in alpha-Minimum Essential Media (α-MEM) at 37° C. in a 5% $CO_2$ environment. After 6, 12 and 24 hours incubation, media was removed and cells were washed with PBS. A solution of 75% ethanol, 20% acetic acid, and 5% water fixed cells to the culture surface and opened cell materials. The fixative was removed after 1 minute, and the cells were washed three times with media and once more with PBS.

An immunofluorescent stain applied to the cells aided in their identification. The technique employed involved indirect staining of vimentin, a cytoplasmic antigen. Since the fixative had permealized the cell material, antibody was allowed into the cytoplasm and the cell may be stained. Monoclonal anti-vimentin |mouse IgM isotype, Sigma Immunochemicals, lot #099F4802| was diluted in media in a 1:200 volume:volume ratio and introduced to the cells and polymer for 30 minutes. This process was followed by 3 washes in media and one in PBS. A fluorescent labeled conjugate of anti-vimentin [anti-mouse IgM, Sigma, lot

012H8855] was used to mark cells to which the antibody was bound. Samples were then examined on a confocal laser microscope (Zeiss Axioskop fluorescent microscope connected to a Bio-Rad MRC 600 argon/krypton laser unit).

Positive and negative controls were also examined. Cells were grown on TCPS in the absence of PLAGA. These samples as well as polymer on which no cells had been cultured were stained in the manner outlined above and viewed under the microscope.

In addition to the microscope examination of the cells, cell count experiments were performed. 5000 cells suspended in α-MEM were plated onto 0 and 50% HA samples and TCPS controls and incubated at 37° C. in a 5% $CO_2$ environment. After 6, 12 and 24 h incubation, three specimens at each HA load and three controls were washed with trypsin for 2 minutes, flushed with media three times and PBS once to remove cells from the polymer. The cells were then resuspended in 10 ml of media and counted using a hemocytometer.

Adhesion of MC-3T3 cells to the polymer was studied using confocal laser microscopy. A central section of each polymer was removed before samples were examined microscopically to image the cells which had been growing in the interior of the matrix. The immunofluorescent stain provided contrast between the cells and the polymer matrix such that cells could be identified. Levels of black and white contrast in confocal laser microscope photographs provides different information than equivalent color contrast in SEM pictures. In photographs of the confocal laser microscope field, white, grey and black are levels of fluorescence, not depth. Cells, which had a fluorescent label, appeared as bright white patches and polymer, which had no such label, as the dark background. Photographs of cells growing in 50% HA samples after 6, 12 and 24 h incubation respectively, with a magnification factor of 20×, showed that isolated groups of cells had become attached to the polymer in the 6 h after plating. Given the low cell density at this time point, the contrast between cell and polymer is very distinct. At this level of cell adhesion and field fluorescence, the structure of the polymer itself is discernible. Pores in the matrix appear as the darkest spots in the photograph. Cells had grown in a ring around the largest pore found in the right half of the picture.

After 12 h incubation on the polymer, cells had started to proliferate, with a significant increase in the number of cells over 12 h. The white areas in the photograph correspond to locations of high cell density, the grey areas to regions of low cell density, and the black areas to the polymer surface. Groups of cells were no longer isolated in clusters, but had spread over more of the surface area of the polymer, and more of the field fluoresced. This trend continued as time passed. After 24 hr, much of the photograph is grey as a result of the low cell density over most of the polymer surface. The polymer had become obscured by the fluorescence of the cells. Dense colonies of cells caused the areas of bright fluorescence in the central portion of the photograph.

0% HA matrices were also examined in the confocal studies. However, polymer specimens at this ceramic load level exhibited a high degree of autofluorescence. As a result, it was difficult to capture a meaningful image of these surfaces.

Cell count studies contradicted the expected pattern of increased cell adhesion with time, a pattern suggested by the confocal studies. These results indicate that cell attachment to polymer and TCPS had become complete between 6 and 12 h. By 24 h there was no increase in the number of cells on either the polymer or the controls. This indicated that cell attachment had become complete within the first 12 h but that proliferation had not yet begun. The confocal work also showed that cells were able to move through the pores and attach themselves on the inside of the polymer structure.

Modifications and variations of the present invention will be obvious to those skilled in the art. Such modifications and variations are intended to come within the scope of the appended claims.

We claim:

1. A porous composite comprising hydroxyapatite particles having a diameter in the range of between approximately 10 microns and 100 microns mixed with a biodegradable, biocompatible polymer wherein the pores have a diameter in the range of between approximately 100 and 250 microns.

2. The composite of claim 1 wherein the biodegradable, biocompatible polymer is selected from the group consisting of polyanhydrides, polyhydroxy acids, polyorthoesters, polyphosphazenes, blends thereof, and copolymers thereof.

3. The composite of claim 1 further comprising osteoblasts.

4. The composite of claim 1 wherein the hydroxyapatite is selected from the group consisting of natural and synthetic hydroxyapatite, bone, cementum, dentin, enamel, tricalcium phosphate, calcium phosphate ($CaPO_4$), and combinations thereof.

5. The composite of claim 1 further comprising a biologically active material selected from the group consisting of antibiotics, chemotherapeutics, bone cell inducers and bone cell stimulators.

6. A process for treating a bone defect comprising implanting at the site of the defect a porous composite comprising hydroxyapatite particles having a diameter in the range of between approximately 10 microns and 100 microns mixed with a biodegradable, biocompatible polymer wherein the pores have a diameter in the range of between approximately 100 and 250 microns.

7. The process of claim 6 wherein the polymer is selected from the group consisting of polyanhydrides, polyhydroxy acids, polyorthoesters, polyphosphazenes, and blends and copolymers thereof.

8. The process of claim 6 further comprising seeding the composite with osteoblasts prior to implantation.

9. The process of claim 6 wherein the hydroxyapatite is selected from the group consisting of natural and synthetic hydroxyapatite, bone, cementum, dentin, enamel, tricalcium phosphate, calcium phosphate ($CaPO_4$), and combinations thereof.

10. The process of claim 6 further comprising administering at the site of implantation a biologically active material selected from the group consisting of antibiotics, chemotherapeutics, bone cell inducers and bone cell stimulators.

11. The composite of claim 1 wherein the hydroxyapatite comprises organic material and ions.

12. The process of claim 6 wherein the hydroxyapatite comprises organic material and ions.

\* \* \* \* \*